United States Patent [19]

Moll et al.

[11] Patent Number: 5,078,718

[45] Date of Patent: Jan. 7, 1992

[54] MULTI-PART METHOD AND APPARATUS FOR REMOVING PRE-PLACED PROSTHETIC JOINTS AND PREPARING FOR THEIR REPLACEMENT

[75] Inventors: Frederic H. Moll, San Francisco; Milton B. Mccoll, Los Altos Hills; F. T. Watkins, Menlo Park; Charles Gresl, San Francisco, all of Calif.

[73] Assignee: Origin Medsystems, Inc., San Mateo, Calif.

[21] Appl. No.: 510,145

[22] Filed: Apr. 17, 1990

[51] Int. Cl.$^5$ ............................................. A61F 5/04
[52] U.S. Cl. ........................................ 606/86; 606/99
[58] Field of Search .................. 606/86, 87, 88, 92, 606/93, 94, 99, 100; 411/383, 384, 386, 412, 413, 178, 397; 623/66, 23

[56] References Cited

U.S. PATENT DOCUMENTS

| | | | |
|---|---|---|---|
| 824,983 | 7/1906 | Farrington | 411/397 |
| 1,907,495 | 5/1933 | Brunski | 411/397 |
| 2,243,717 | 5/1941 | Moreira | 606/104 |
| 3,334,624 | 8/1967 | Schneider | 606/100 |
| 4,100,626 | 7/1978 | White | 606/86 |
| 4,222,382 | 9/1980 | Antonsson | 128/92 |
| 4,248,232 | 2/1981 | Engelbrecht et al. | 128/305 |
| 4,399,813 | 8/1983 | Barber | 128/92 |
| 4,463,753 | 8/1984 | Gustilo | 128/92 |
| 4,476,861 | 10/1984 | Dimakos | 128/303 |
| 4,612,922 | 9/1986 | Barber | 128/92 |
| 4,616,638 | 10/1986 | Griggs | 606/104 |
| 4,686,971 | 8/1987 | Harris | 128/92 |
| 4,702,236 | 10/1987 | Tarabichy | 606/86 |
| 4,834,081 | 5/1989 | van Zile | 128/92 |
| 4,838,264 | 6/1989 | Bremer | 606/86 |
| 4,858,601 | 8/1989 | Glisson | 606/104 |

FOREIGN PATENT DOCUMENTS 0312957 4/1989 European Pat. Off. .............. 606/86

OTHER PUBLICATIONS

"Möglichkeiten der Anwendug von Ultraschallwerkzeug bei Endoprothesenwechsel", E. Nieder, E. Engelbrecht, U. Röder und E. Strickle, DER CHIRURG, 1979.

Techniques in Orthopedics, "Revision of Total Hip and Knee", Lawrence D. Dorr, M.D., pp. 14-22.

"Revision in Surgery for Failed, Monseptic Total Hip Arthroplasty-The Femoral Side", William H. Harris, M.D., pp. 8-20.

Primary Examiner—Danton D. DeMille
Assistant Examiner—Michael Brown
Attorney, Agent, or Firm—Limbach, Limbach & Sutton

[57] ABSTRACT

A method and apparatus for removing a pre-placed prosthetic joint from a bone cavity and conditioning the cavity for receipt of a replacement joint. The pre-placed joint is first pulled from the mantle of hardened cement holding it within the cavity, thus leaving a cavity within the mantle. A mass of fluid cement is then placed within the cement cavity, after which a pulling tool is inserted into the fluid cement and the fluid cement is permitted to cure to bond with the hardened cement and form an integral mass. The pulling tool has detachable sections or sleeves, each with grip forming elements on its exterior and structure to connect a slap-hammer to its proximal end. Tension is then applied to the each section to remove the section and the cement mantle surrounding it from the bone cavity. The process is repeated for each section until all of the cement mantle is removed.

21 Claims, 8 Drawing Sheets

MULTI-PART METHOD AND APPARATUS FOR REMOVING PRE-PLACED PROSTHETIC JOINTS AND PREPARING FOR THEIR REPLACEMENT

BACKGROUND OF THE INVENTION

This application relates to U.S. applications Ser. No. 255,650, filed Oct. 11, 1988, and continuation-in-part application Ser. No. 467,742, and application Ser. No. 467,724, both filed Jan. 19, 1990.

1. Field of the Invention

As do the other applications referenced above, the present invention relates to the replacement of pre-placed prosthetic joints and more particularly to a method and apparatus for removing the cement mantle used to secure the pre-placed joint in place.

The replacement of a failed prosthetic joint, such as a hip or knee joint, requires that both the prosthetic appliance and the cement mantle holding it in place within the bone cavity be removed. The old prosthetic device is usually easily removed using a slap-hammer, since its surface is smooth and separable from the underlying cement mantle. The cement mantle, however, is tightly adherent to the surrounding bone and generally remains so adhered, even after the prosthetic device is removed.

2. Description of the Relevant Art

In the prior art, removal of the adhered cement mantle was performed by chipping the mantle away with a hammer and chisel. This and related methods are tedious and allow the possibility of fracturing the underlying bone.

Methylmethacrylate cement is the most accepted type of cement used to secure prosthetic joint appliances to bone. Old hardened methylmethacrylate cement is capable of being partially dissolved and softened by the application of new like fluid cement thereto. The resulting composite of old and new cement cures into an integral bonded composite in a matter of minutes.

In the method of the invention described in application Ser. No. 255,650, a mass of new fluid methylmethacrylate cement is placed in contact with the hardened mantle of old methylmethacrylate cement desired to be removed. A pulling appliance is then imbedded within the fluid cement and the mass of cement is permitted to cure and harden, thus forming a bond between the appliance and the mantle of old cement. Tension is then applied to the pulling mantle to pull the appliance and the entire bonded mantle from the bone.

However, even in that method, the force needed to pull the entire mantle from the bone may damage the bone. Continuation-in-part application Ser. No. 467,742 concerns the improvement or removing the bonded mantle from the bone in a number of pieces to reduce the amount of force needed to remove each piece to avoid such damage to the surrounding bone.

Application Ser. No. 467,724 involves a kit of components for use with the method of removing the mantle in pieces, to simplify the procedure and make it essentially foolproof.

SUMMARY OF THE INVENTION

The present invention similarly provides improved tools for use with the technique of removing the mantle in two or more pieces, rather than in a single unit. The pulling tools of the present invention all comprise rigid posts of cylindrical configuration surrounded in whole or in part by cylindrical sleeves having outer surfaces with grip forming elements. In some embodiments, the sleeves are of multiple sections. The proximal end of each tool or sleeve portion is provided with means to secure a slap-hammer thereto.

In varying embodiments, the post may be removed from the sleeves, and then a slap hammer connected to each sleeve section in turn to remove a portion of the mantle. Alternatively, the sleeve sections may be connected to the slap hammer with the post still inserted, and the post itself used to remove the final portion of the mantle.

A principle object of the present invention is to provide an improved method and apparatus for removing a cement mantle from adhered condition within a bone cavity.

Another object of the invention is to provide such a method and apparatus which enables the mantle to be removed in pieces with a minimum of force to avoid damage to the surrounding bone.

Still another object of the invention is to provide such a method and apparatus which avoids the necessity of chipping away at the mantle to effect its removal.

Another and more specific object of the invention is to provide an improved tool for use with such a method which allows removal of the mantle quickly and efficiently, with a minimum of steps.

The features and advantages described in the specification are not all inclusive, and many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

FIGS. 1A through 4H of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1A:
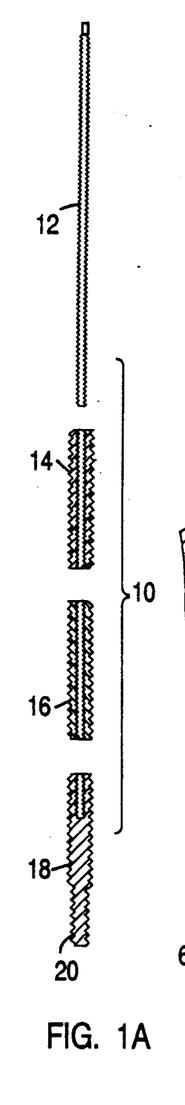
FIG. 1A is an elevational view illustrating a first pulling tool constructed according to one embodiment of the present invention.

As shown in FIG. 1A, the first pulling tool 10 is comprised of a post 12 and sleeve sections 14, 16 and 18. When assembled, first pulling tool 10 has a length and cross-section sufficient to enable it to be extended to the bottom of the cavity in the mantle in which it is intended to be used, without imparting lateral forces to the wall of the cavity. The tool may be fabricated of any suitable high tensile strength corrosion-resistant material, such as stainless steel.

The pulling tool provides a rigid post 12 of cylindrical configuration having a helical screw thread formed around it. The proximal end is adapted for receipt in the socket of a slap-hammer. The sleeve sections 14, 16, and 18 are also cylindrical, with grip forming elements on the outside and an internal threaded passageway along the long axis of each section into which the post 12 may be screwed. In sleeve sections 14 and 16 the threaded passageway goes completely through the section along its long axis, while in sleeve section 18, which is intended to be used at the end of post 12, the threaded passageway goes only part of the way through the section.

The distal end 20 of sleeve section 18 is of reduced diameter compared to the proximal end. As can be seen from FIG. 10, the distal end of the enlarged diameter portion of the sleeve section 18 serves as a stop to limit the degree to which the pulling instrument may penetrate the cavity in the cement mantle. Its reduced cross-section assures that it may be inserted as far down into the cavity in the cement mantle as is necessary to remove the entire mantle, as will become more apparent from the following description of the method.

Figures 2A, 2B:
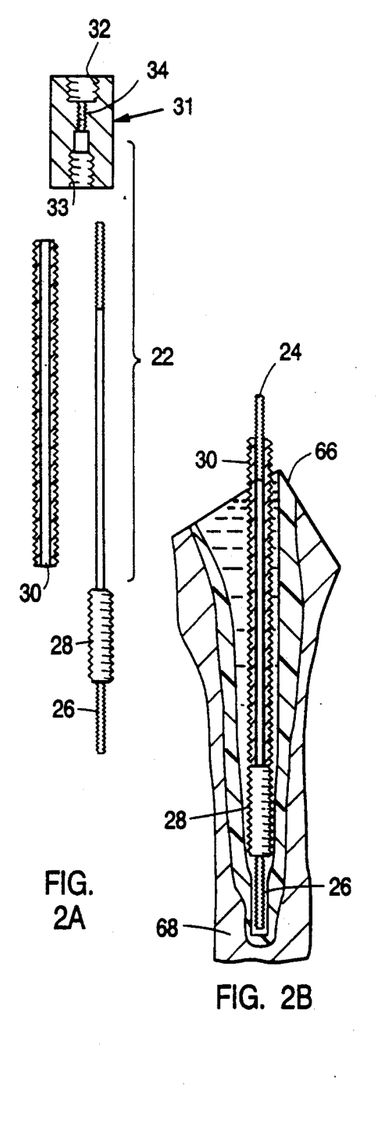
FIG. 2A is an elevational view of a second pulling tool constructed according to one embodiment of the present invention.
FIG. 2B is a cross-sectional elevational view similar to FIG. 1B, illustrating the step of placing the second pulling tool within the fluid cement.

FIG. 2A shows the second pulling tool 22. When assembled, it is of a similar configuration as the first pulling tool 10, with the exception that it is separated into two portions, a post 24 and a sleeve 30. A distal portion 26, which corresponds to distal portion 20 of sleeve section 18 of the first pulling tool 10, is fixed to and extends from the post portion 24. Immediately adjacent to distal portion 26 is a stop section 28 of greater diameter than the remainder of post 24. Distal section 26 and stop section 28 have grip forming elements in the form of screw threads on their outside cylindrical surface. The remainder of post 24, above stop section 28, is smooth, except for a helical screw thread at the proximal end of post 24.

Sleeve 30 has a smooth passageway along its long axis, sized so that post 24 may be inserted into sleeve 30. The sleeve 30 also has a helical screw thread formed on its outside cylindrical surface. As shown, the outside diameter of sleeve 30 is the same as that of stop section 28, although this is not required. Similarly, as shown, sleeve 30 is approximately as long as the portion of post 24 above the stop section 28, although it may be longer.

A connector 31 is also illustrated in FIG. 2A. At its proximal end, connector 31 has a threaded receptacle 32 for receipt of a slap hammer. At its distal end, connector 31 has a threaded receptacle 33 for receipt of the helical screw thread on sleeve 30. Axially aligned with this receptacle 33 and further indented in connector 31 is another smaller threaded receptacle 34 for receipt of the screw thread on the proximal end of post 24.

Figures 3A, 3B, 3C:
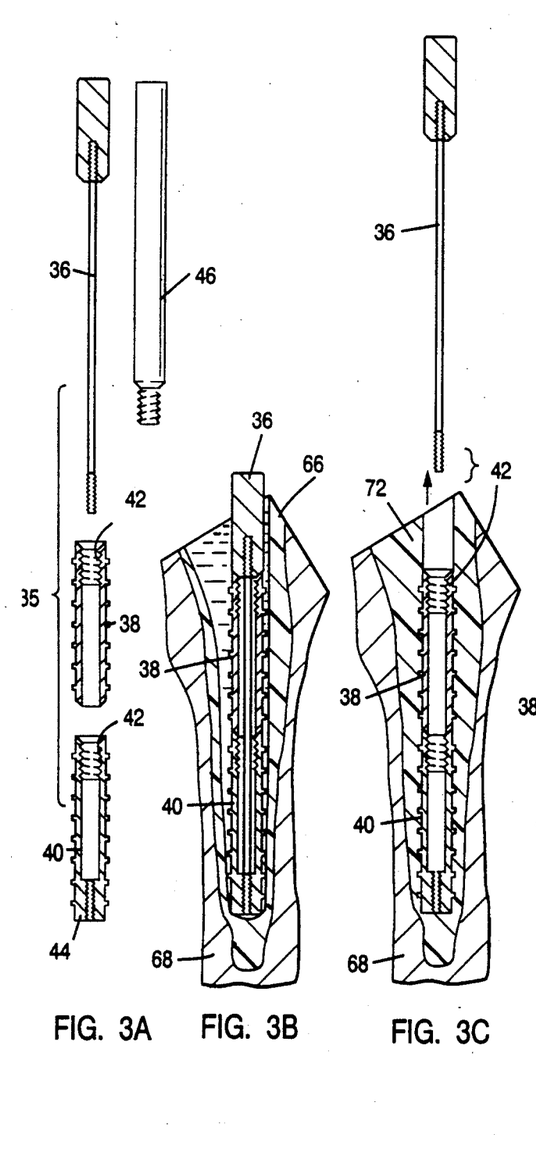
FIG. 3A is an elevational view of a third pulling tool constructed according to one embodiment of the present invention.
FIG. 3B is a cross-sectional elevational view similar to FIG. 1B, illustrating the step of placing the third pulling tool within the fluid cement.
FIG. 3C is a cross-sectional elevational view similar to FIG. 3B, illustrating the step of removing the post from the sleeve and leaving the sleeve in the hardened cement.

FIG. 3A shows the third pulling tool 35. In this case, the post 36 has threaded portion at the distal end, and an enlarged handle at the proximal end. Sleeve sections 38 and 40 are both cylindrical, with grip forming elements on their outside surfaces and interior passageways through which post 36 may be extended. The passageway in each sleeve section is threaded for a short portion 42 at the proximal end of the sleeve section. In addition, the distal end 44 of the passageway in sleeve section 40, designed for use at the distal end of post 36, is narrow and threaded to accommodate the threaded portion at the distal end of post 36. A connecting tool 46 is provided to secure the sleeve sections to the slap hammer. The tool 46 has a distal end that is threaded to be received in the threaded portion 42 of the passageway in each sleeve. The remainder of the connecting tool 46 is smooth, and is of a diameter smaller than the outside diameter of the sleeve portions.

Figures 4A, 4B, 4C, 4D:
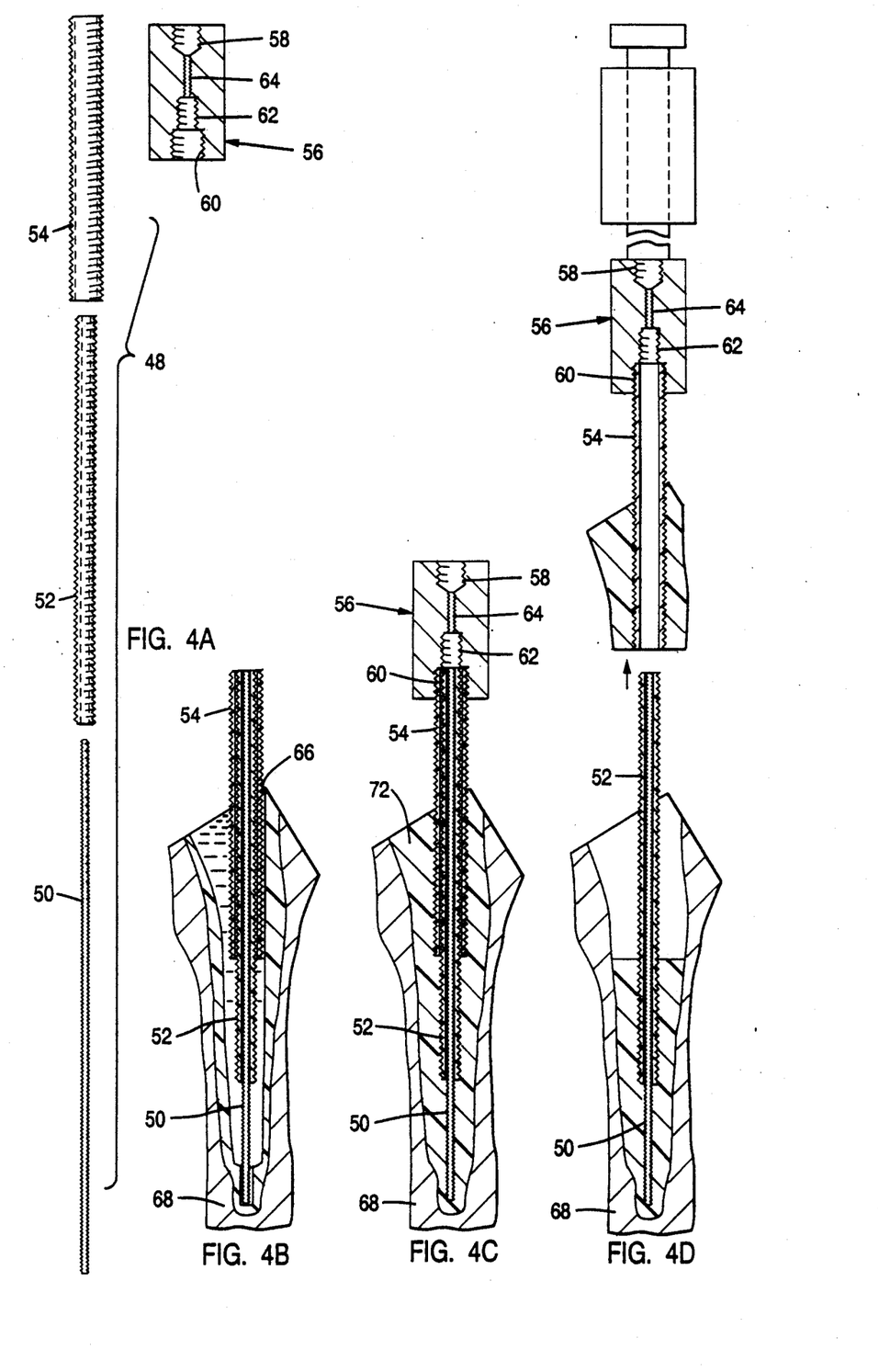
FIG. 4A is an elevational view of a fourth pulling tool constructed according to one embodiment of the present invention.
FIG. 4B is a cross-sectional elevational view similar to FIG. 1B, illustrating the step of placing the fourth pulling tool within the fluid cement.
FIG. 4C is a cross-sectional elevational view similar to FIG. 4B, illustrating the step of attaching a connector to the first sleeve section.
FIG. 4D is a cross-sectional elevational view similar to FIG. 4C, illustrating the step of using a slap-hammer to apply tension to the cement mantle through the first section of the sleeve and removing a portion of the cement mantle from the femur.

FIG. 4 shows a fourth pulling tool 48. It is comprised of a post 50, an inner sleeve 52, and an outer sleeve 54, all cylindrical in shape, and all having helical threads on the exterior surface. The post 50 again is of a length and diameter appropriate to reach the bottom of the cavity in the hardened mantle without impacting upon the wall of the cavity. Inner sleeve 52 is shorter than post 50 and of a diameter greater than post 50, and has an internal passageway along its long axis which is slightly greater in diameter than post 50 so that post 50 may be extended through the passageway. Similarly, outer sleeve 54 is shorter than inner sleeve 52, but of a diameter greater than inner sleeve 52, with an internal passageway along its long axis of slightly greater diameter than inner sleeve 52, so that inner sleeve 52 may be extended through the passageway.

As in the second pulling tool, a connector 56 is also illustrated in FIG. 4A. At its proximal end, connector 56 has a threaded receptacle 58 for receipt of a slap hammer. At its distal end, connector 56 has a threaded receptacle 60 for receipt of the helical screw thread on outer sleeve 54. Axially aligned with this receptacle 60 and further indented in connector 56 is a smaller threaded receptacle 62 for receipt of the screw thread on the inner sleeve 52. Indented still further, again axially aligned with receptacles 60 and 62, is a still smaller threaded receptacle 64 for receipt of the post 50.

Figure 1B:
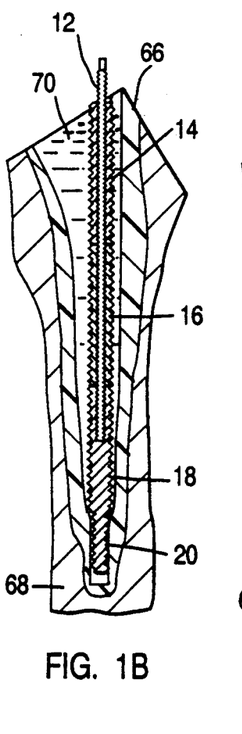
FIG. 1B is a cross-sectional elevational view of the upper femur of a leg, wherein a femoral component of a prosthetic hip joint has been removed from a cement mantle and a new mass of cement injected into the cavity left by removal of the component, showing the step of placing the first pulling tool within the fluid cement in the cavity.

FIGS. 1B through 1H sequentially illustrate the steps of one method in removing a cement mantle 66 from a femur 68. The femur is illustrated after the previous femoral component of a prosthetic joint has been removed therefrom and the trochanter of the femur has been removed to facilitate the method. After the first pulling tool 10 has been assembled by screwing post 12 into the three sleeve sections 14, 16, and 18, FIG. 1B shows the first pulling tool 10 inserted into the cement mass 70 while the mass is still in a fluid state. This is achieved by pushing or screwing the tool into the mass to the point where the distal end 20 engages the bottom of the mantle 66, which may be determined by feel, and creates a passageway within the cement mass 70. The insertion of the tool 10 into the fluid mass of cement 70 is carried out in a slow controlled fashion so as to avoid the creation of voids within the mass. This is not a problem, since it takes approximately ten minutes for the mass to cure to a hardened state.

Figure 1C:
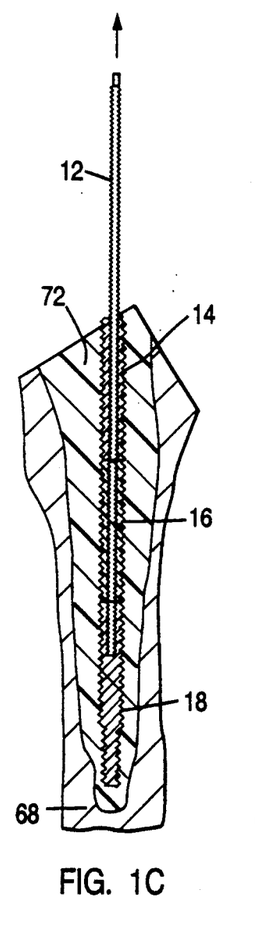
FIG. 1C is a cross-sectional elevational view similar to FIG. 1B, illustrating the step of partly removing the post of the first pulling tool from the sleeve after the cement has hardened.
Figure 1D:
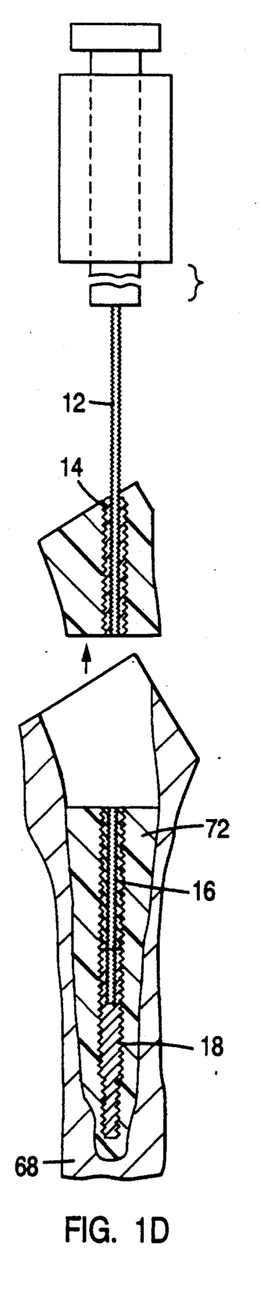
FIG. 1D is a cross-sectional elevational view similar to FIG. 1C, illustrating the step of using a slap-hammer to apply tension to the cement mantle through the post and a section of the sleeve and removing a portion of the cement mantle from the femur.

After the mass of cement 70 has cured to a hardened integral state with the mantle 66 to form an integral cement mass 72, the post 12 of first pulling tool 10 is partly removed by unscrewing it from the threaded passageways in second and third sleeve sections 16 and 18, as shown in FIG. 1C, so that post 12 is attached only to first sleeve section 14. As shown in FIG. 1D, the slap-hammer is then threadably secured to the proximal end of the post 12, and used to apply impact tension to the pulling tool. Another characteristic of the methylmethacrylate cement is that it has no significant tensile strength. The hardened mass of cement thus shears at the lowest point where the grip forming elements of the first sleeve section 14 engage the cement mass 72. The use of the slap-hammer thus pulls the post 12, the first sleeve section 14, and the portion of the mantle surrounding the first sleeve section 14 from the femur as a unit, leaving behind that portion of the mantle below the lowest point where the grip forming elements of the first sleeve section 14 engage the cement mass 72.

Figure 1E:
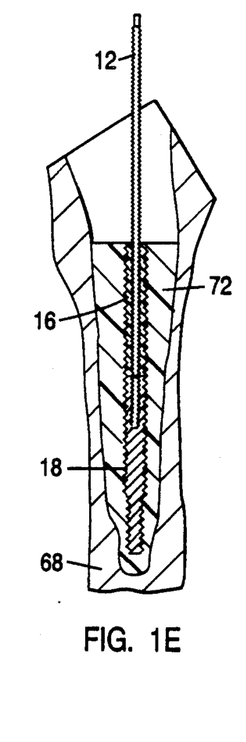
FIG. 1E is a cross-sectional elevational view similar to FIG. 1D, illustrating the step of reinserting the post into a second section of the sleeve located in the portion of the cement mantle remaining in the femur.
Figure 1F:
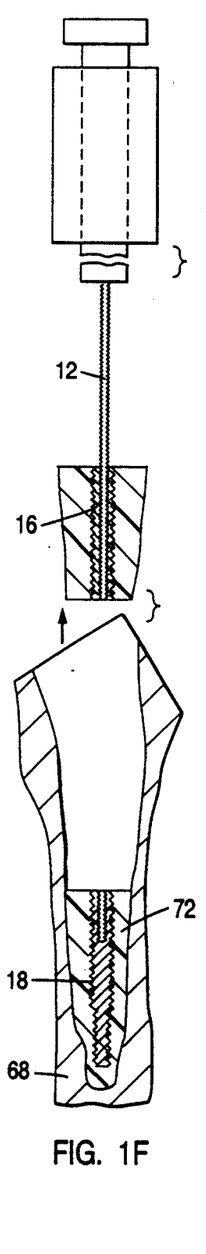
FIG. 1F is a cross-sectional elevational view similar to FIG. 1E, illustrating the step of using a slap-hammer to apply tension to the cement mantle through the post and a section of the sleeve and removing a second portion of the cement mantle from the femur.
Figure 1G:
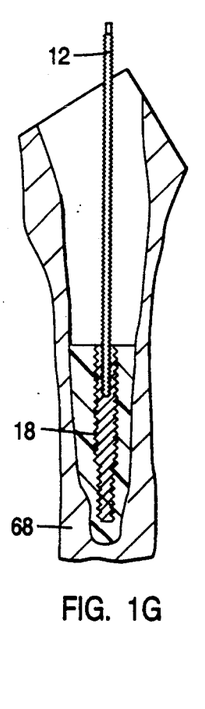
FIG. 1G is a cross-sectional elevational view similar to FIG. 1F, illustrating the step of reinserting the post into the final section of the sleeve located in the portion of the cement mantle remaining in the femur.
Figure 1H:
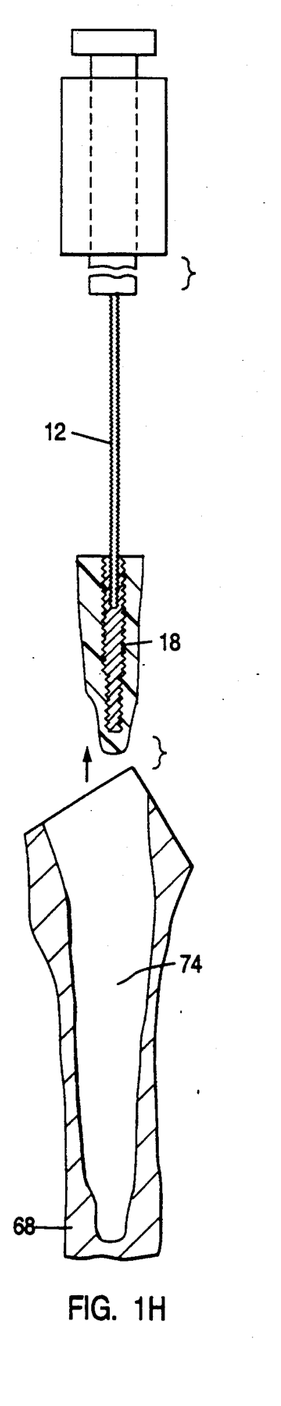
FIG. 1H is a cross-sectional elevational view similar to FIG. 1G, illustrating the step of using a slap-hammer to apply tension to the cement mantle through the post and the last section of the sleeve and removing the final portion of the cement mantle from the femur.

Next, as shown in FIG. 1E, the post 12 is reinserted into second sleeve section 16 by screwing it into the threaded passageway in second sleeve section 16. Then, as shown in FIG. 1F, the slap hammer is again attached to the post 12 and a second portion of the mantle is removed. Finally, as shown in FIGS. 1G and 1H, the pulling tool is reinserted into third sleeve portion 18 by screwing it into the passageway in third sleeve section 18, and the slap-hammer is used to remove the final portion of the cement. This step leaves the original bone cavity, designated 74, within the femur in a clean state. Thereafter, a new prosthetic joint may be cemented into the bone cavity.

FIGS. 2A through 2H sequentially illustrate the steps of an alternative method of removing the cement mantle 66 by use of the second pulling tool 22, which is shown in FIG. 2A. The prior prosthesis is removed as previously described, and second pulling tool 22 is assembled by sliding sleeve 30 onto the proximal end of post 24. A mass of fluid cement 70 is then injected into the cavity, and second pulling tool 22 is inserted into the cement mass 70 while it is still in a fluid state, as shown in FIG. 2B. The threaded exterior surface of sleeve 30 defines a threaded passageway 76 in the cement.

Figure 2C:
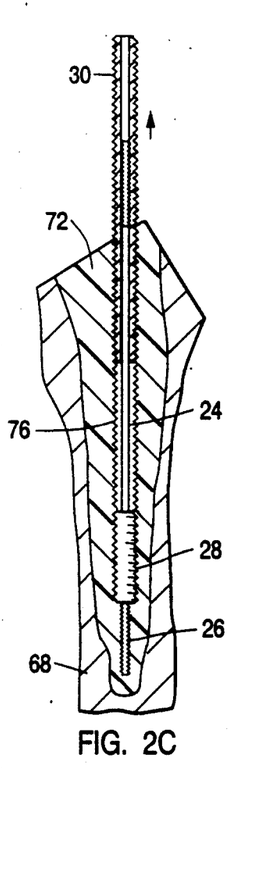
FIG. 2C is a cross-sectional elevational view similar to FIG. 2B, illustrating the step of partly removing the sleeve from the hardened cement.
Figure 2D:
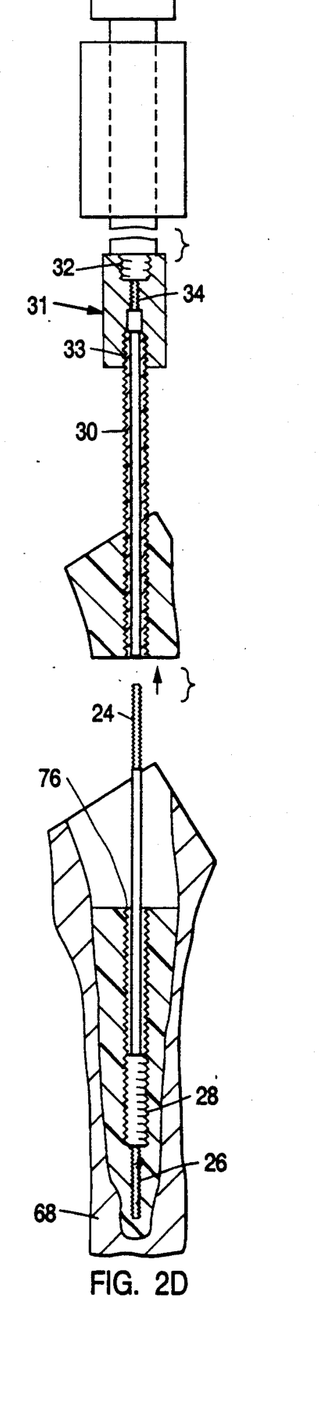
FIG. 2D is a cross-sectional elevational view similar to FIG. 2C, illustrating the step of using a slap-hammer to apply tension to the cement mantle through the sleeve and removing a portion of the cement mantle from the femur.

After the cement hardens, the sleeve 30 of the second pulling tool 68 is partly removed by unscrewing it from the threaded passageway 76, as shown in FIG. 2C. Since sleeve 30 merely slides onto post 24, unscrewing sleeve 30 does not disturb post 24. Next, as shown in FIG. 2D, the slap-hammer is secured to the proximal end of the sleeve 30 by use of the connector 31. Sleeve 30 is screwed into receptacle 33, and the slap hammer is then used to apply impact tension to sleeve 30, thus shearing off the methylmethacrylate cement at the point of deepest penetration of the sleeve 30, as in the prior embodiment.

Figure 2E:
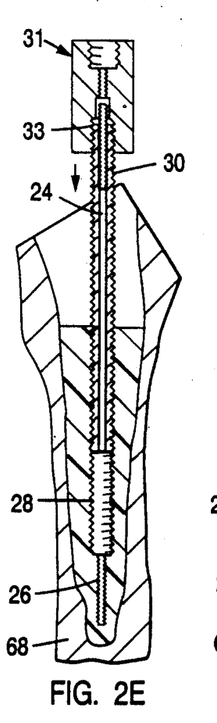
FIG. 2E is a cross-sectional elevational view similar to FIG. 2D, illustrating the step of reinserting the sleeve into the portion of the cement mantle remaining in the femur.
Figure 2F:
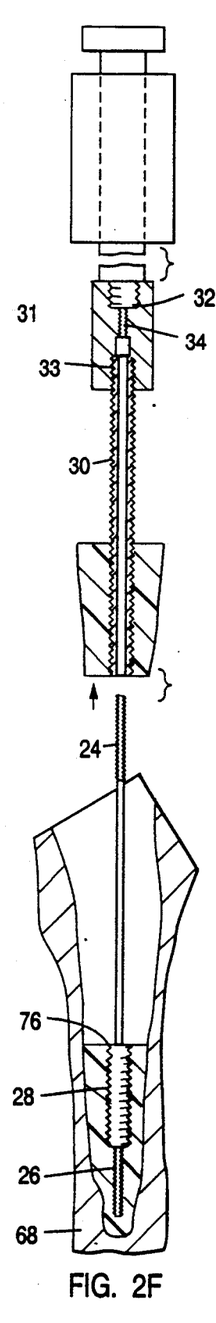
FIG. 2F is a cross-sectional elevational view similar to FIG. 2E, illustrating the step of using a slap-hammer to apply tension to the cement mantle through the sleeve and removing a second portion of the cement mantle from the femur.
Figure 2G:
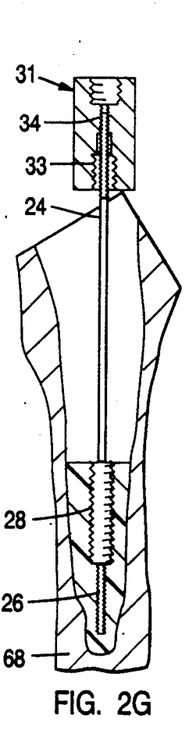
FIG. 2G is a cross-sectional elevational view similar to FIG. 2F, illustrating the step of attaching a connector to the post located in the portion of the cement mantle remaining in the femur.
Figure 2H:
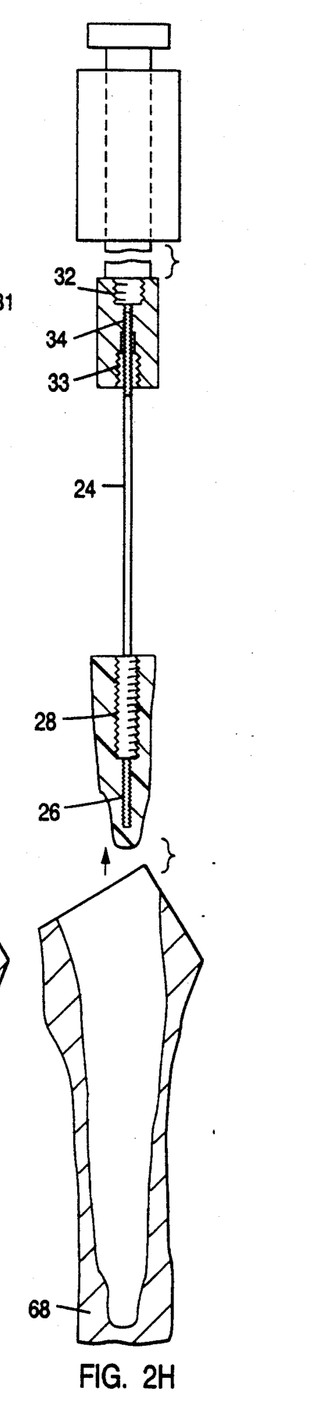
FIG. 2H is a cross-sectional elevational view similar to FIG. 2G, illustrating the step of using a slap-hammer to apply tension to the cement mantle through the post and removing the final portion of the cement mantle from the femur.

The sleeve 30 is then reinserted into threaded passageway 76 in the mantle 72 by screwing it in back to its original depth, and again sleeve 30 is screwed into receptacle 33 on connector 31, as shown in FIG. 2E. Impact tension is again applied by the slap hammer and a second portion of the mantle 72 removed as shown in FIG. 2F. Finally, as shown in FIG. 2G, the proximal end of the post 24 is screwed into receptacle 34 of connector 31, and the remaining portion of the mantle is removed by use of the slap hammer as shown in FIG. 2H.

FIGS. 3A through 3G sequentially illustrate the steps of another alternative method of removing the cement mantle 66 by use of the third pulling tool 35, which is shown in FIG. 3A. The prior prosthetic appliance is again removed, and third pulling tool 35 is assembled by sliding first sleeve section 38 onto the distal end of post 36, and then sliding second sleeve section 40 onto the distal end of post 36 and securing it in place by screwing threaded portion at the distal end of post 36 into the distal end 44 of the passageway in second sleeve section 40. Fluid cement 70 is then injected into the cavity, and while it is still in a fluid state, third pulling tool 35 is inserted into the cement mass 70, as shown in FIG. 3B.

Figures 3D, 3E:
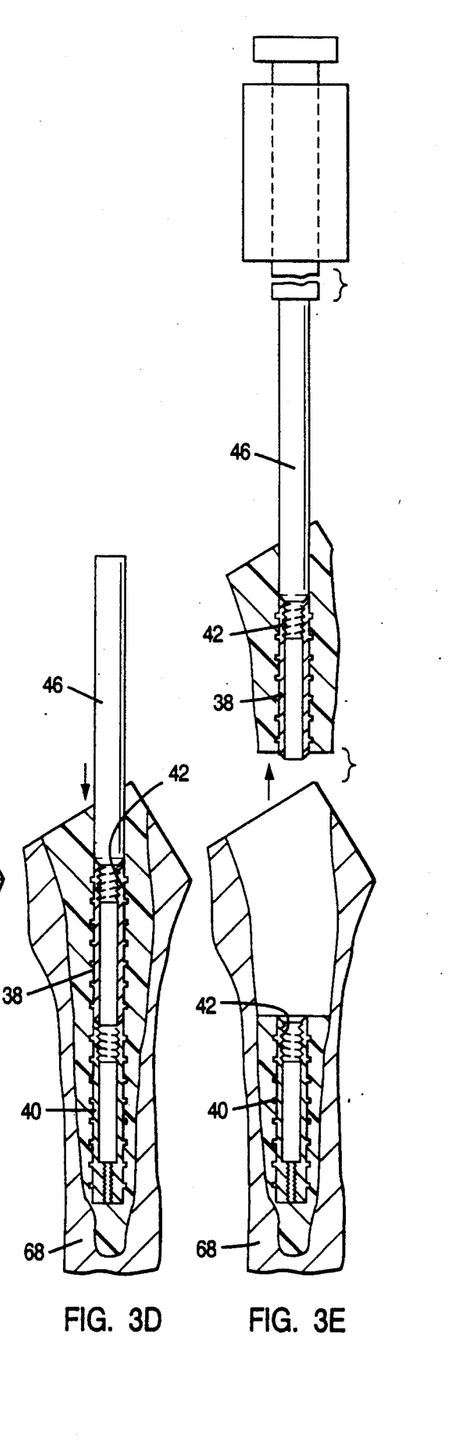
FIG. 3D is a cross-sectional elevational view similar to FIG. 3C, illustrating the step of attaching a connector to the first sleeve section.
FIG. 3E is a cross-sectional elevational view similar to FIG. 3D, illustrating the step of using a slap-hammer to apply tension to the cement mantle through the first section of the sleeve and removing a portion of the cement mantle from the femur.

After the cement hardens into integral mass 72, post 36 is detached by unscrewing the distal threaded end of post 36 from the threaded distal end 44 of second sleeve section 40 and removed. Next, as shown in FIG. 3D, the connecting tool 46 is screwed into the threaded portion 42 at the proximal end of first sleeve section 38, as shown in FIG. 3D. The slap-hammer is then secured to the proximal end of the connecting tool 46 and used to apply impact tension to it, again shearing off the methylmethacrylate cement at the point of deepest penetration of the first sleeve portion 38, as shown in FIG. 3E.

Figure 3F:
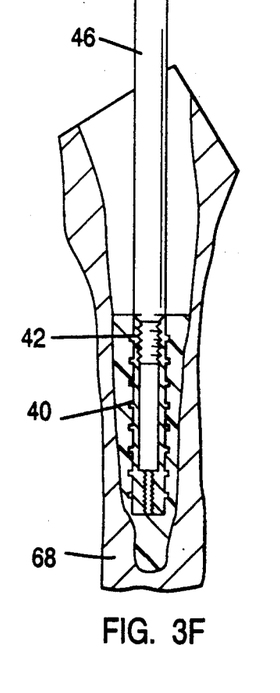
FIG. 3F is a cross-sectional elevational view similar to FIG. 3E, illustrating the step of attaching the connector to the second section of the sleeve in the portion of the cement mantle remaining in the femur.
Figure 3G:
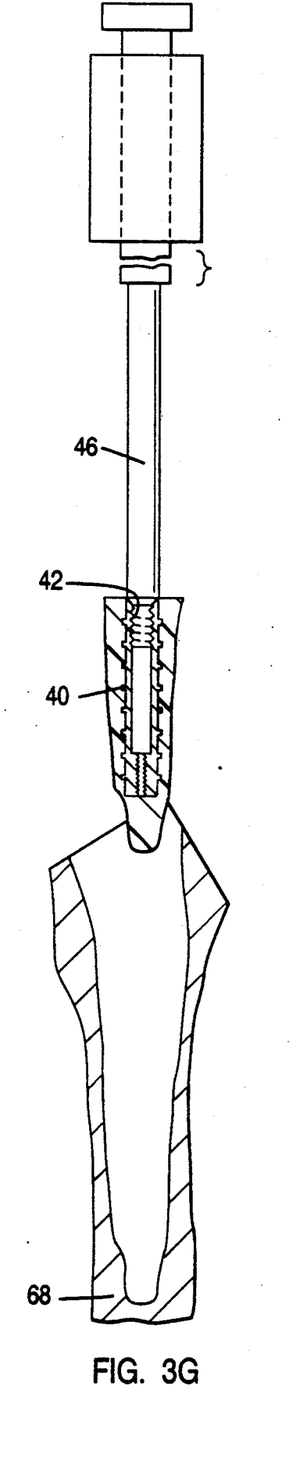
FIG. 3G is a cross-sectional elevational view similar to FIG. 3F, illustrating the step of using a slap-hammer to apply tension to the cement mantle through the second section of the sleeve and removing a second and final portion of the cement mantle from the femur.

Finally, connecting tool 46 is attached to the second sleeve section 40 by again screwing it into threaded portion 42, as shown in FIG. 3F, the slap-hammer is attached to connecting tool 46, and the remaining portion of the mantle is removed as shown in FIG. 3G.

FIGS. 4A through 4H sequentially illustrate the steps of another alternative method of removing the cement mantle 66 by use of the fourth pulling tool 48, which is shown in FIG. 4A. The fourth pulling tool 48 is assembled by sliding inner sleeve 52 over post 50, and outer sleeve 54 over inner sleeve 52, with the proximal ends of each component aligned. As before, fourth pulling tool 48 is inserted into the fluid mass of cement 70 before it hardens, as shown in FIG. 4B.

Once the cement hardens into integral mass 72, connector 56 is attached to outer sleeve 54 by screwing the proximal end of outer sleeve 54 into threaded receptacle 60, as shown in FIG. 4C. The slap hammer is then secured to the proximal end of connector 56 and used to apply impact tension to outer sleeve 54, thus shearing off the cement at the point of deepest penetration of outer sleeve 54, as shown in FIG. 4D. Since as in the second embodiment the sleeves and post are not attached, this does not disturb the placement of inner sleeve 52 or post 50.

Figures 4E, 4F, 4G, 4H:
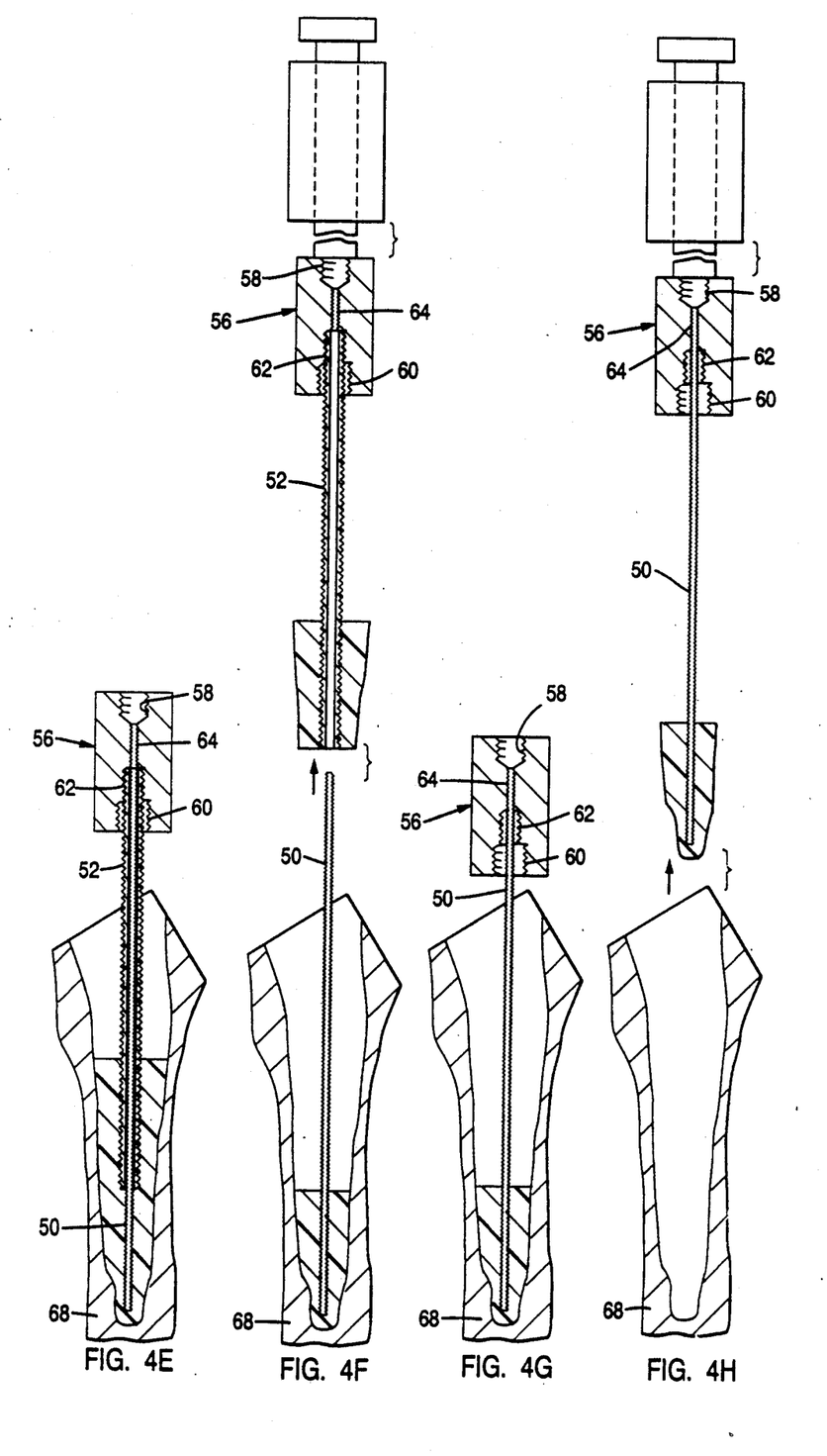
FIG. 4E is a cross-sectional elevational view similar to FIG. 4D, illustrating the step of attaching the connector to the second section of the sleeve in the portion of the cement mantle remaining in the femur.
FIG. 4F is a cross-sectional elevational view similar to FIG. 4E, illustrating the step of using a slap-hammer to apply tension to the cement mantle through the second section of the sleeve and removing a second portion of the cement mantle from the femur.
FIG. 4G is a cross-sectional elevational view similar to FIG. 4F, illustrating the step of attaching the connector to the post in the portion of the cement mantle remaining in the femur.
FIG. 4H is a cross-sectional elevational view similar to FIG. 4G, illustrating the step of using a slap-hammer to apply tension to the cement mantle through the post and removing a third and final portion of the cement mantle from the femur.

Next, connector 56 is attached to inner sleeve 52 by screwing the proximal end of inner sleeve 52 into threaded receptacle 62 as shown in FIG. 4E. The slap hammer is again secured to the connector 56 and again used to apply impact tension to inner sleeve 54, again removing a portion of cement down to the deepest penetration of inner sleeve 52, as shown in FIG. 4F. Finally, post 50 is screwed into receptacle 64 of connector 56 as shown in FIG. 4G, and the slap hammer is used to apply tension to remove the final portion of the mantle as shown in FIG. 4H.

Conclusion

Numerous variations on these embodiments are possible. For example, to prevent the fluid cement from bonding to the pulling tool as it hardens, it is possible to use a light plastic post to form the threaded passageway, even if it is of insufficient strength to serve as the pulling tool, and then replace it with a steel pulling tool of the same configuration once the cement has hardened. Here the plastic post need not have a detachable distal end, even if the pulling tool is of the second or third types described above, since the plastic will be removed and not used in the steps of actually removing the cement mantle. In addition, the process can be broken into even more steps so that smaller pieces of the mantle are removed with each use of the slap-hammer, if this is necessary to insure that the force applied can be kept small enough so as not to damage the surrounding bone.

From the above description, it will be apparent that the invention disclosed herein provides a novel and advantageous method and apparatus for removing preplaced prosthetic joints and preparing for their replacement. The foregoing discussion discloses and describes merely exemplary methods and embodiments of the present invention. As will be understood by those familiar with the art, the invention may be embodied in other specific forms without departing from the spirit or essential characteristics thereof. For example, it is anticipated that the invention may find use in the removal of a cement mantle in other than a joint replacement application and that it may be used in replacing joints other than hip joints. Accordingly, the disclosure of the present invention is intended to be illustrative, but not limiting, of the scope of the invention, which is set forth in the following claims.

We claim:

1. An improved pulling tool for embedment within a cavity in a mass of cement to remove the cement from a recess within a bone, said tool comprising:
   a rigid cylindrical post having proximal and distal ends;
   a rigid cylindrical sleeve comprising a plurality of detached sections, said sleeve having proximal and distal ends and having defined within it a passageway through which the post may be extended and having an exterior surface with grip means thereon or gripping engagement with the cavity in the mass of cement; and, means to releasably secure the cylindrical sleeve to the post whereby the sleeve may be selectively held against axial separation from the post, or released for such separation.

2. An improved pulling tool according to claim 1 wherein said passageway is threaded so that said post may be screwed into said passageway.

3. An improved pulling tool according to claim 2 further comprising means on said proximal end of said post for securing a slap hammer to said post.

4. An improved pulling tool according to claim 2 further comprising a distal tip section which comprises:
 a first rigid cylindrical section having proximal and distal ends, having a threaded recess in its proximal end for receipt of said post and an exterior surface with grip means thereon for gripping engagement with the cavity in the mass of cement; and
 a second rigid cylindrical section of reduced diameter as compared to said first section, which extends axially from the distal end of said first section and which has an exterior surface of grip forming elements.

5. An improved pulling tool according to claim 1 further comprising attachment means in said passageway in each section of the sleeve for attaching each said section to a slap hammer.

6. An improved pulling tool according to claim 5 wherein said attachment means comprises:
 a section of threaded passageway at the proximal end of each section of the sleeve;
 a connector having proximal and distal ends, the distal end being threaded to be received in said sections of threaded passageway; and
 means for attaching the proximal end of said connector to a slap hammer.

7. An improved pulling tool according to claim 1 further comprising a second rigid cylindrical sleeve having proximal and distal ends and having defined within it a passageway of a diameter slightly larger than said sleeve for receipt of said first mentioned sleeve, and having an exterior surface of grip forming elements.

8. An improved pulling tool according to claim 7 further comprising means on said proximal end of said post for securing a slap hammer to said post.

9. An improved pulling tool according to claim 7 further comprising means on said proximal end of said first mentioned sleeve for securing a slap hammer to said sleeve.

10. An improved pulling tool according to claim 7 further comprising means on said proximal end of said second sleeve for securing a slap hammer to said second sleeve.

11. An improved pulling tool for embedment within a cavity in a mass of cement to remove the cement from a recess within a bone, said tool comprising:
 a rigid cylindrical post having proximal and distal ends;
 a rigid cylindrical sleeve having proximal and distal ends and having defined within it a passageway through which the post may be extended and having an exterior surface with grip means thereon for gripping engagement with the cavity in the mass of cement;
 means for releasably secure the cylindrical sleeve to the post whereby the sleeve may be selectively held against axial separation from the post, or released for such separation;
 a distal tip having an exterior surface with grip means thereon for gripping engagement with the cavity in the mass of cement; and
 a cylindrical section immediately adjacent to said distal tip, said cylindrical section having an exterior surface with grip means thereon for gripping engagement with the cavity in the mass of cement.

12. An improved pulling tool according to claim 11 further comprising means on said proximal end of said post for securing a slap hammer to said post.

13. An improved pulling tool according to claim 11 further comprising means on aid proximal end of said sleeve for securing a slap hammer to said sleeve.

14. A method for removing a prosthetic appliance secured in place by a mantle of hardened methylmethacrylate cement received within a bone cavity and conditioning the bone cavity for receipt of a new appliance, comprising the steps of:
 (a) pulling the appliance from the mantle of hardened cement to leave a cement cavity within the mantle;
 (b) providing a pulling tool having a cylindrical post and a cylindrical sleeve of a length shorter than said post surrounding a portion of said post;
 (c) inserting said pulling tool in said cavity;
 (d) injecting a fluid mass of cement into said cavity surrounding said pulling tool;
 (e) permitting said fluid mass of cement to harden around said pulling tool and bond to the hardened mantle;
 (f) applying tension to said sleeve to pull said sleeve and the surrounding portion of the mantle of cement from the bone cavity while leaving a remaining portion of the mantle in the cavity.

15. A method according to claim 14, further comprising the step of applying tension to said post to pull said post and the surrounding portion of the mantle of cement from the bone cavity.

16. A method according to claim 14, wherein the step of providing the pulling tool further comprises providing a second cylindrical sleeve of a length shorter than said post surrounding a second portion of said post, and further comprising the step of applying tension to said second sleeve to pull said second sleeve and the surrounding portion of the mantle of cement from the bone cavity.

17. A method according to claim 16, further comprising the step of applying tension to said post to pull said post and the surrounding portion of the mantle of cement from the bone cavity.

18. A method according to claim 16, further comprising the step of removing said post from said sleeves prior to the step of applying tension to said sleeve to pull said sleeve and the surrounding portion of the mantle of cement from the bone cavity.

19. A method for removing a prosthetic appliance secured in place by a mantle of hardened methylmethacrylate cement received within a bone cavity and conditioning the bone cavity for receipt of a new appliance, comprising:
 (a) pulling the appliance from the mantle of hardened cement to leave a cement cavity within the mantle:
 (b) providing a pulling tool having a cylindrical post, a first cylindrical sleeve of a length shorter than said post surrounding a portion of said post, and a second cylindrical sleeve of a length shorter than said first sleeve surrounding a portion of said first sleeve;

(c) inserting said pulling tool in said cavity;

(d) injecting a fluid mass of cement into said cavity surrounding said pulling tool;

(e) permitting said fluid mass of cement to harden around said pulling tool and bond to the hardened mantle;

(f) applying tension to said second sleeve to pull said second sleeve and the surrounding portion of the mantle of cement from the bone cavity while leaving a remaining portion of the mantle in the cavity;

(g) applying tension to said first sleeve to pull said first sleeve and the surrounding portion of the mantle of cement from the bone cavity.

20. A method according to claim 19, further comprising the step of removing said post from said sleeves prior to the step of applying tension to said sleeve to pull said sleeve and the surrounding portion of the mantle of cement from the bone cavity.

21. A method according to claim 19, further comprising the step of applying tension to said post to pull said post and the surrounding portion of the mantle of cement from the bone cavity.

* * * * *